(12) United States Patent
Karthikeyan et al.

(10) Patent No.: US 11,077,260 B2
(45) Date of Patent: Aug. 3, 2021

(54) FLOW CONTROL PLUG SECUREMENT

(71) Applicant: Becton, Dickinson and Company, Franklin Lakes, NJ (US)

(72) Inventors: Sakthivel Karthikeyan, Tamil Nadu (IN); Sudarsan Srinivasan, North Brunswick, NJ (US)

(73) Assignee: Becton, Dickinson and Company, Franklin Lakes, NJ (US)

( * ) Notice: Subject to any disclaimer, the term of this patent is extended or adjusted under 35 U.S.C. 154(b) by 608 days.

(21) Appl. No.: 15/896,257

(22) Filed: Feb. 14, 2018

(65) Prior Publication Data

US 2019/0247642 A1    Aug. 15, 2019

(51) Int. Cl.
| | |
|---|---|
| *A61M 5/36* | (2006.01) |
| *A61M 39/10* | (2006.01) |
| *A61M 39/20* | (2006.01) |
| *A61M 39/16* | (2006.01) |
| *A61M 25/00* | (2006.01) |
| *A61M 39/04* | (2006.01) |

(52) U.S. Cl.
CPC ............ *A61M 5/36* (2013.01); *A61M 39/105* (2013.01); *A61M 39/1011* (2013.01); *A61M 39/162* (2013.01); *A61M 25/0097* (2013.01); *A61M 39/04* (2013.01); *A61M 2039/1027* (2013.01); *A61M 2039/1072* (2013.01); *A61M 2039/1077* (2013.01); *A61M 2039/1083* (2013.01); *A61M 2039/205* (2013.01)

(58) Field of Classification Search
CPC .. A61M 39/105; A61M 5/36; A61M 39/1011; A61M 39/162; A61M 25/0097; A61M 39/04; A61M 2039/1027; A61M 2039/1072; A61M 2039/1077; A61M 2039/1083; A61M 2039/205; A61M 2039/0227; A61M 2005/2492; A61M 5/348; A61M 2205/586; A61M 39/20; A61M 39/16; A61M 5/165; A61M 25/0606

See application file for complete search history.

(56) References Cited

U.S. PATENT DOCUMENTS 4,095,810 A    6/1978   Kulle
4,123,091 A *  10/1978  Cosentino ........... F16L 37/0847
                                                         285/39

(Continued)

FOREIGN PATENT DOCUMENTS

DE    3515665    5/1986
EP    0081655    6/1983

(Continued)

*Primary Examiner* — Theodore J Stigell
(74) *Attorney, Agent, or Firm* — Kirton & McConkie; Craig Metcalf; Kevin Stinger

(57) ABSTRACT

A catheter system may include a luer adapter, which may include an outer surface having threading or a recess. The catheter system may also include a flow control plug, which may include a proximal end and a distal end. The proximal end of the flow control plug may include a filter element permeable to air and not to blood. The distal end of the flow control plug may include a cylinder and a taper-shaped luer tip spaced apart from the cylinder. An inner surface of the cylinder may include a protrusion engaged in a snap-fit with the recess or corresponding threading mated with the threading.

5 Claims, 14 Drawing Sheets

(56) References Cited

U.S. PATENT DOCUMENTS

| | | | | |
|---|---|---|---|---|
| 4,752,292 A * | 6/1988 | Lopez | ................ | A61M 39/1011 604/244 |
| 5,066,286 A * | 11/1991 | Ryan | ....................... | A61M 5/34 604/240 |
| 5,269,771 A * | 12/1993 | Thomas | .............. | A61M 39/045 251/149.1 |
| 5,591,143 A * | 1/1997 | Trombley, III | ....... | A61M 39/10 604/534 |
| 5,620,427 A * | 4/1997 | Werschmidt | .......... | A61M 39/10 137/516.13 |
| 8,066,669 B2 | 11/2011 | Christensen et al. | | |
| 8,066,670 B2 * | 11/2011 | Cluff | .................... | A61M 39/20 604/126 |
| 8,377,040 B2 * | 2/2013 | Burkholz | ............ | A61M 1/3659 604/533 |
| 8,991,436 B2 | 3/2015 | Birch | | |
| 10,695,550 B2 * | 6/2020 | Gardner | ................ | A61M 39/20 |
| 2009/0299337 A1 | 12/2009 | Groppi et al. | | |
| 2011/0009717 A1 | 1/2011 | Davis et al. | | |
| 2011/0212294 A1 | 9/2011 | Kato | | |
| 2012/0111368 A1 | 5/2012 | Rahimy et al. | | |
| 2013/0165867 A1 * | 6/2013 | Isaacson | ........... | A61M 39/0606 604/256 |
| 2013/0197485 A1 * | 8/2013 | Gardner | .............. | A61M 39/162 604/533 |
| 2014/0249477 A1 | 9/2014 | Grimm et al. | | |
| 2015/0265500 A1 | 9/2015 | Russo et al. | | |
| 2017/0216572 A1 | 8/2017 | Stenzel et al. | | |
| 2017/0239443 A1 * | 8/2017 | Abitabilo | .......... | A61M 25/0693 |

FOREIGN PATENT DOCUMENTS

| | | |
|---|---|---|
| EP | 813884 | 12/1997 |
| WO | 95/26675 | 10/1995 |
| WO | 2012/009457 | 1/2012 |

* cited by examiner

FLOW CONTROL PLUG SECUREMENT

BACKGROUND OF THE INVENTION

Infusion therapy is one of the most common health care procedures. Hospitalized, home care, and other patients receive fluids, pharmaceuticals, and blood products via a vascular access device inserted into the vascular system. Infusion therapy may be used to treat an infection, provide anesthesia or analgesia, provide nutritional support, treat cancerous growths, maintain blood pressure and heart rhythm, or many other clinically significant uses.

Infusion therapy is facilitated by a vascular access device. The vascular access device may access a patient's peripheral or central vasculature. The vascular access device may be indwelling for short term (days), moderate term (weeks), or long term (months to years). The vascular access device may be used for continuous infusion therapy or for intermittent therapy.

A common vascular access device is a catheter that is inserted into a patient's vein. The catheter length may vary from a few centimeters for peripheral access to many centimeters for central access. The catheter may be inserted transcutaneously or may be surgically implanted beneath the patient's skin. The catheter may have a single lumen or multiple lumens for infusion of many fluids simultaneously.

One example of a catheter system that includes a catheter is the BD NEXIVA™ Closed IV (intravenous) Catheter System, by Becton, Dickinson and Company. This system includes an over-the-needle, peripheral intravascular catheter, integrated extension tubing, a Y-adapter, a slide clamp, a flow control plug, a Luer access port, and a passive needle-shielding mechanism.

The design of the BD NEXIVA™ IV Catheter System can be described as a closed system since it protects clinicians or operators from blood exposure during the catheter insertion procedure. Since the needle is withdrawn through a septum that seals, after the needle has been removed and both ports of the Y-adapter are closed, blood is contained within the NEXIVA™ device during catheter insertion. The pressure exerted on the needle as it passes through the septum wipes blood from the needle, further reducing potential blood exposure. The clamp on the integrated extension tubing is provided to eliminate blood exposure when the flow control plug is replaced with another vascular access device such as an infusion set connection or a Luer access port.

A current procedure of initiating the use of a catheter system such as the BD NEXIVA™ Closed IV Catheter System is as follows. A device operator will insert the needle into the vasculature of a patient and wait for flashback of blood to travel into the device to confirm that the needle is properly located within the vasculature of the patient. The blood travels into and along the catheter of the device because a flow control plug permits air to escape the device as blood enters the device. In some instances, after an operator confirms proper placement, the operator may clamp the catheter system to halt the progression of blood through the catheter system, remove the flow control plug, replace the flow control plug with another vascular access device such as an infusion set connection or a Luer access port, unclamp the catheter system, flush the blood from the catheter system back into the vasculature of the patient, and re-clamp the catheter system.

BRIEF SUMMARY OF THE INVENTION

The present disclosure relates generally to a flow control plug and related devices, systems, and methods. In some embodiments, the flow control plug may be secured to a luer adapter of a catheter system in a secure manner, which may prevent accidental uncoupling of the flow control plug from the luer adapter prior to use. If the flow control plug prematurely uncouples from the luer adapter, contamination of the flow control plug may result, making the flow control plug unable to be used. In some embodiments, the flow control plug may also be secured to the luer adapter in a fluid-tight manner, which may importantly prevent leakage of fluid from the catheter system. In some embodiments, the flow control plug may also include one or more features that facilitate attachment of the flow control plug to the luer adapter during assembly or prior to use, including, for example, grip elements and/or flexible arms. In some embodiments, the flow control plug may include one or more features that reduce an axial force and torque necessary to make a connection between the flow control plug and the luer adapter.

As used in the present disclosure, the term "distal" refers to a portion of the IV catheter system or component thereof that is farther from a user, and the term "proximal" refers to a portion of the IV catheter system or component thereof that is closer to the user. As used in the present disclosure, the term "user" may refer to a clinician, doctor, nurse, or any other care provider and may include support personnel.

In some embodiments, the catheter system may include one or more of the following: a catheter adapter, a catheter extending distally from the catheter adapter, a needle extending through the catheter and beyond a distal tip of the catheter when the needle is in an insertion position, the luer adapter, extension tubing, and the flow control plug. In some embodiments, the catheter adapter may include a side port, which may be coupled to the extension tubing. In some embodiments, the catheter adapter may include a septum, which may be disposed in a needle channel through which the needle travels in response to being retracted. In some embodiments, a fluid pathway of the catheter adapter may include one or more of the following: a lumen of the catheter adapter distal to the septum, the side port, the extension tubing, and the luer adapter. In some embodiments, the luer adapter may be connectable to another vascular access device, such as blood withdrawal and/or infusion means.

In some embodiments, the catheter system may include an intravenous (IV) catheter system. In some embodiments, the catheter system may include an integrated or a closed catheter system, such as, for example, the BD NEXIVA™ Closed IV Catheter System, the BD NEXIVA™ DIFFUSICS™ Closed IV Catheter System, the BD SAF-T-INTIMA™ Closed IV Catheter System, or the Becton Dickinson PEGASUS™ Safety Closed IV Catheter System.

In some embodiments, the luer adapter may include a single port adapter, a dual port adapter, a Y-adapter, or another suitable type of luer adapter. In some embodiments, the luer adapter may include an outer surface, which may include a recess. In some embodiments, the luer adapter may be coupled to a catheter adapter via extension tubing. In some embodiments, the catheter system may include a flow control plug, which may include a proximal end and a distal end. In some embodiments, the proximal end of the flow control plug may include a filter element, which may be permeable to air and not permeable to blood. In some embodiments, the distal end of the flow control plug may include a cylinder and a taper-shaped luer tip spaced apart from the cylinder.

In some embodiments, an inner surface of the cylinder may include a protrusion engaged in a snap-fit with the recess, which may secure the flow control plug to the luer adapter. In some embodiments, the outer surface of the luer adapter may include threading. In some embodiments, the distal end of the flow control plug may include corresponding threading, which may be mated with the threading to secure the flow control plug to the luer adapter.

In some embodiments, the cylinder may include multiple slots, which may form multiple arms of the cylinder. The arms may be disposed between the slots. In some embodiments, the slots may extend through the cylinder. In some embodiments, an inner surface of one of the arms may include the protrusion. In some embodiments, multiple of the arms may each include another protrusion, which may engage in a snap-fit with the recess or with another recess in the outer surface of the luer adapter. For example, the slots may include a first slot and a second slot, and the arms may include a first arm and a second arm. In some embodiments, the first slot and the second slot may be disposed between the first arm and the second arm. In some embodiments, an inner surface of the first arm may include the protrusion. In some embodiments, an inner surface of the second arm may include another protrusion. In some embodiments, the other protrusion may be engaged in a snap-fit with the recess or with another recess of the outer surface of the luer adapter.

In some embodiments, the distal end may include a stepped surface. In some embodiments, the distal end may extend outwardly from the proximal end to form the stepped surface. In some embodiments, the slots may extend through the stepped surface. In some embodiments, the stepped surface may be annular.

In some embodiments, an outer surface of the cylinder may include one or more first grip elements. For example, outer surfaces of one or more of the arms may include one or more first grip elements. In some embodiments, the first grip elements may include ribs, which may be oriented longitudinally with respect to the flow control plug. In some embodiments, an outer surface of the proximal end may include one or more second grip elements. In some embodiments, the second grip elements may include ribs, which may be oriented longitudinally with respect to the flow control plug. In some embodiments, the cylinder may include a first number of the first grip elements and/or the outer surface of the proximal end may include a second number of the second grip elements. In some embodiments, the second number may be greater than the first number. In some embodiments, a width of each of the first grip elements may be greater than a width of each of the second grip elements.

In some embodiments, a method of securing the flow control plug to the catheter system for shipment may include providing the catheter system and/or coupling the flow control plug to the luer adapter of the catheter system before shipping the catheter system to a destination. In some embodiments, coupling the flow control plug to the luer adapter of the catheter system before shipping the catheter system to the destination includes engaging the recess with the protrusion in a snap-fit or mating the threading to the corresponding threading.

It is to be understood that both the foregoing general description and the following detailed description are exemplary and explanatory and are not restrictive of the invention, as claimed.

BRIEF DESCRIPTION OF THE SEVERAL VIEWS OF THE DRAWINGS

Example embodiments will be described and explained with additional specificity and detail through the use of the accompanying drawings in which.

DETAILED DESCRIPTION OF THE INVENTION

The presently preferred embodiments of the present invention will be best understood by reference to the drawings, wherein like reference numbers indicate identical or functionally similar elements. It will be readily understood that the components of the present invention, as generally described and illustrated in the figures herein, could be arranged and designed in a wide variety of different configurations. Thus, the following more detailed description, as represented in the figures, is not intended to limit the scope of the invention as claimed, but is merely representative of presently preferred embodiments of the invention.

Figure 1:
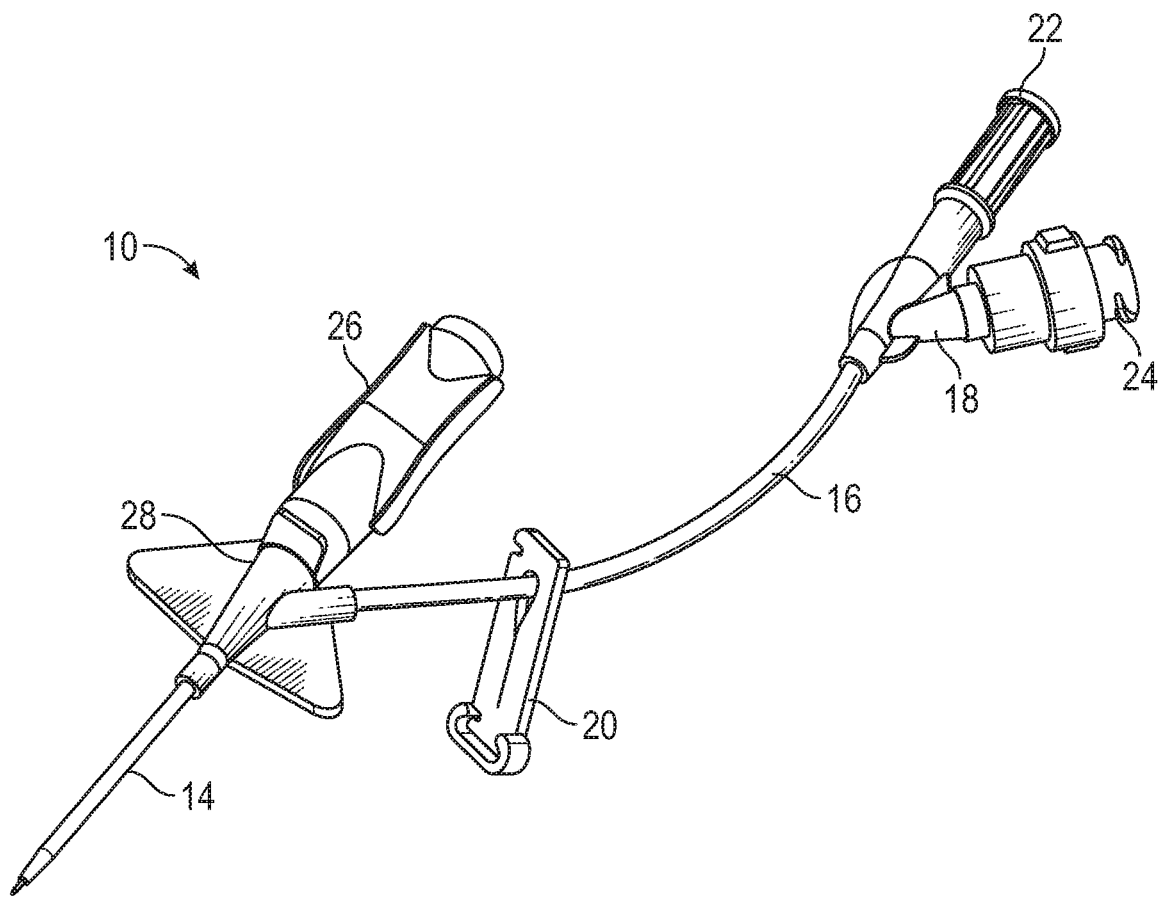
FIG. 1 is an upper perspective view of an example catheter system, according to some embodiments.
Figure 2A:
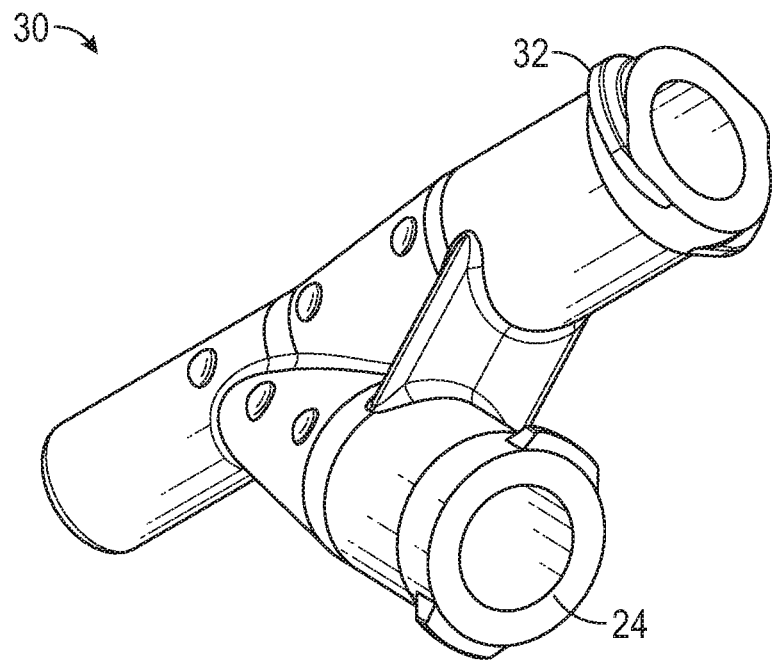
FIG. 2A is an upper perspective view of an example threaded luer adapter, according to some embodiments.
Figure 2B:
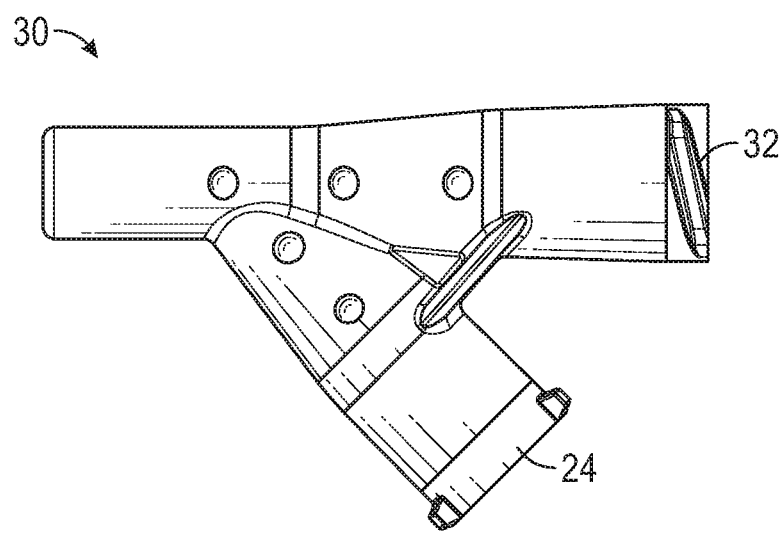
FIG. 2B is a top view of the threaded luer adapter of FIG. 2A, according to some embodiments.
Figure 2C:
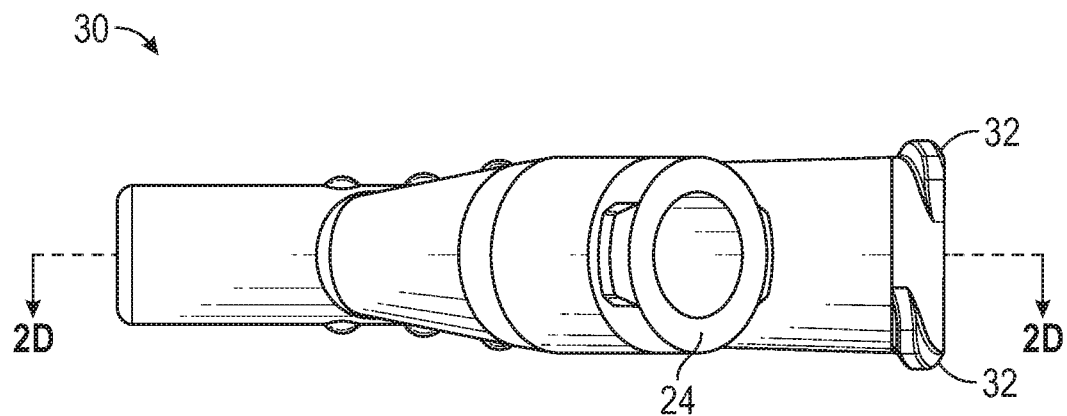
FIG. 2C is a side view of the threaded luer adapter of FIG. 2A, according to some embodiments.
Figure 2D:
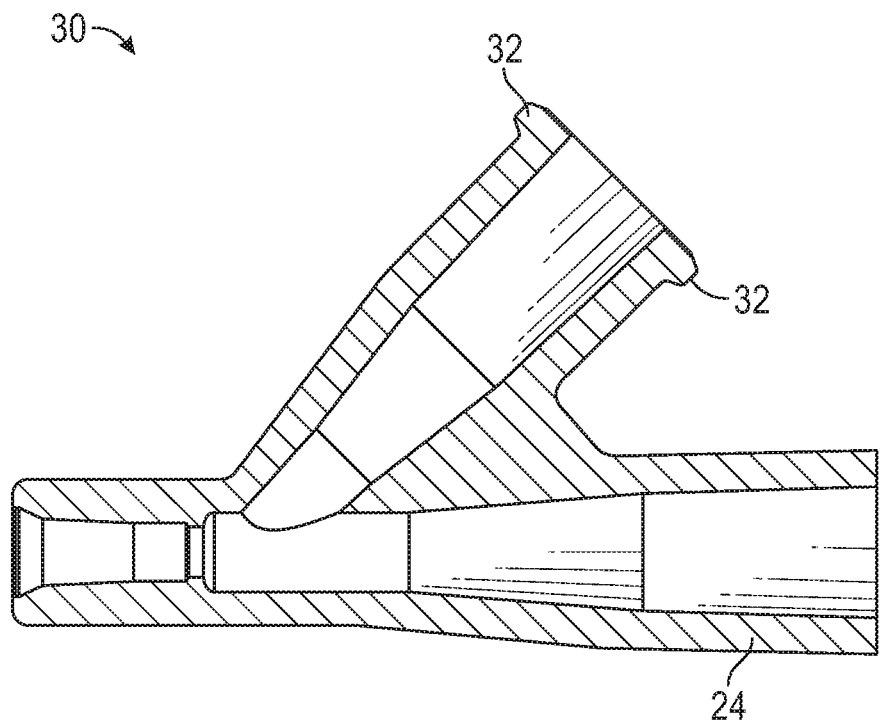
FIG. 2D is a cross-sectional view of the threaded luer adapter of FIG. 2A, along the line 2D-2D of FIG. 2C, according to some embodiments.
Figure 2E:
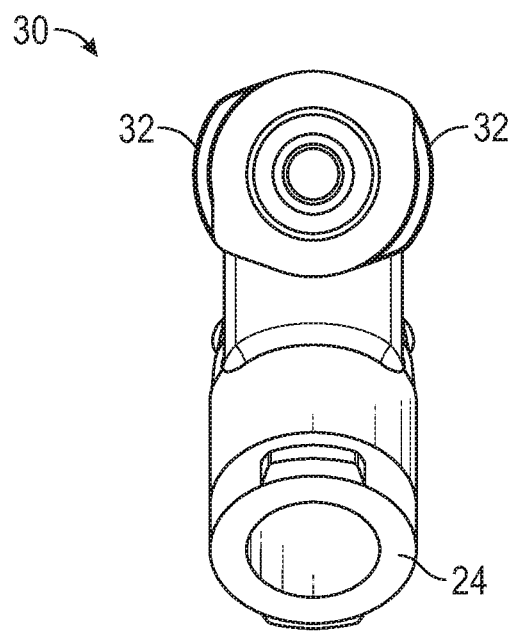
FIG. 2E is a proximal end view of the threaded luer adapter of FIG. 2A, according to some embodiments.

Referring now to FIG. 1, a catheter system 10, such as, for example, the BD NEXIVA™ Closed IV (intravenous) Catheter System, by Becton, Dickinson and Company, is used to communicate fluid with the vascular system of a patient. An example of the catheter system 10, as shown in FIG. 1, includes an introducer needle 12; an over-the-needle, peripheral intravascular catheter 14 made from polyurethane; an integrated extension tubing 16 with a Y-adapter 18 and slide clamp 20; a flow control plug 22; a Luer access port 24; a passive needle-shielding mechanism 26; and a catheter adapter 28 from which the catheter 14 extends. In some embodiments, any adapter used to connect two or more vascular access devices may be used in place of the Y-adapter 18.

The catheter system 10 is a closed system since it protects a user from blood exposure during the catheter 14 insertion procedure. Since the needle 12 is withdrawn through a septum that seals after the needle 12 has been removed and both ports of the Y-adapter 18 are closed, blood is contained within the catheter system 10 during catheter 14 insertion. The pressure exerted on the needle 12 as it passes through the septum wipes blood from the needle 12, further reducing potential blood exposure. The slide clamp 20 on the integrated extension tubing 16 is provided to eliminate blood exposure when the flow control plug 22 is replaced with another vascular access device such as an infusion set connection or another Luer access port 24.

As mentioned above, a current procedure of initiating the use of the extravascular system 10 is as follows. The user may insert the needle 12 into the vasculature of a patient and wait for flashback of blood to travel into the catheter system 10 to confirm that the needle 12 is properly located within the vasculature of the patient. The blood travels into and along the catheter 14 in the space between the needle 12 and the catheter 14. This occurs because a flow control plug 22 permits air to escape the catheter system 10 as blood enters the catheter system 10. After an operator confirms proper placement, and after adequate venting of the catheter system 10 has occurred, the user may clamp extension tubing 16 to halt the progression of blood through the catheter 14, remove the flow control plug 22, replace the flow control plug 22 with another vascular access device such as an infusion set connection or a Luer access port similar or identical to Luer access port 24. In some instances, the user may then unclamp the extension tubing 16, flush the blood from the catheter 14 back into the vasculature of the patient, and re-clamp the extension tubing 16. Alternate flow control plugs, luer adapters, and venting procedures are desired and will be discussed with reference to the figures following FIG. 1.

Referring now to FIG. 2A-2E, an example Y-adapter 30 of the catheter system 10 is illustrated, according to some embodiments. In some embodiments, any adapter used to connect two or more vascular access devices may be used in place of the Y-adapter 30. As illustrated in FIGS. 2A-2E, in some embodiments, an outer surface of the Y-adapter 30 may include one or more threads 32. In some embodiments, a second port of the Y-adapter 30 may include the outer surface having the threads 32. Thus, in some embodiments, both the Luer access port 24 and the second port of the Y-adapter may be threaded.

Figure 3A:
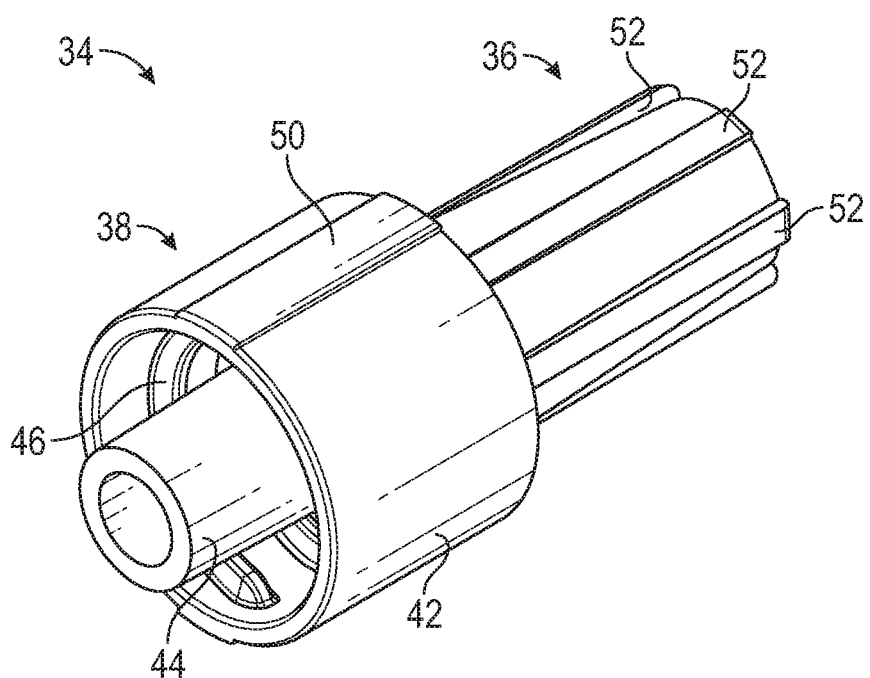
FIG. 3A is an upper perspective view of an example threaded flow control plug, according to some embodiments.
Figure 3B:
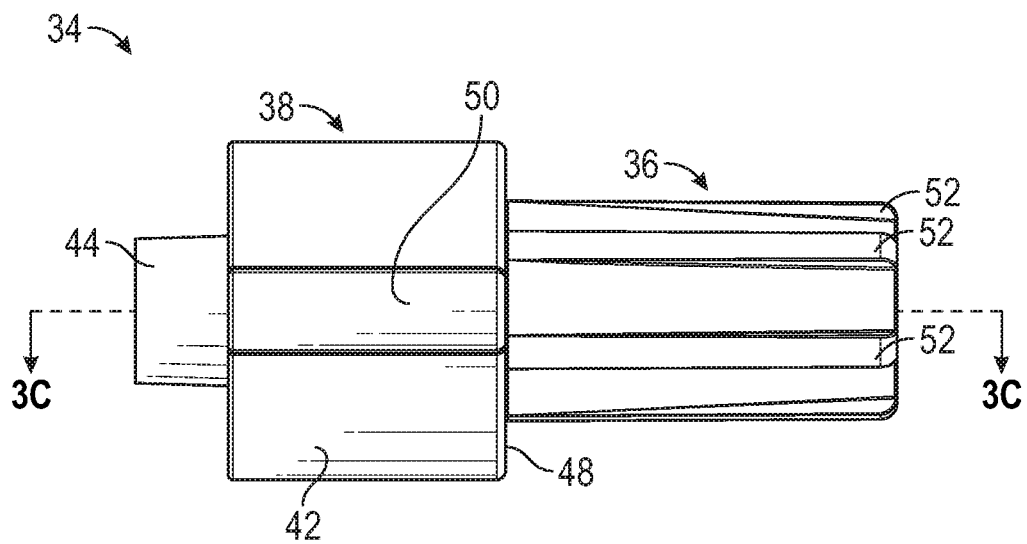
FIG. 3B is a top view the threaded flow control plug of FIG. 3A, according to some embodiments.
Figure 3C:
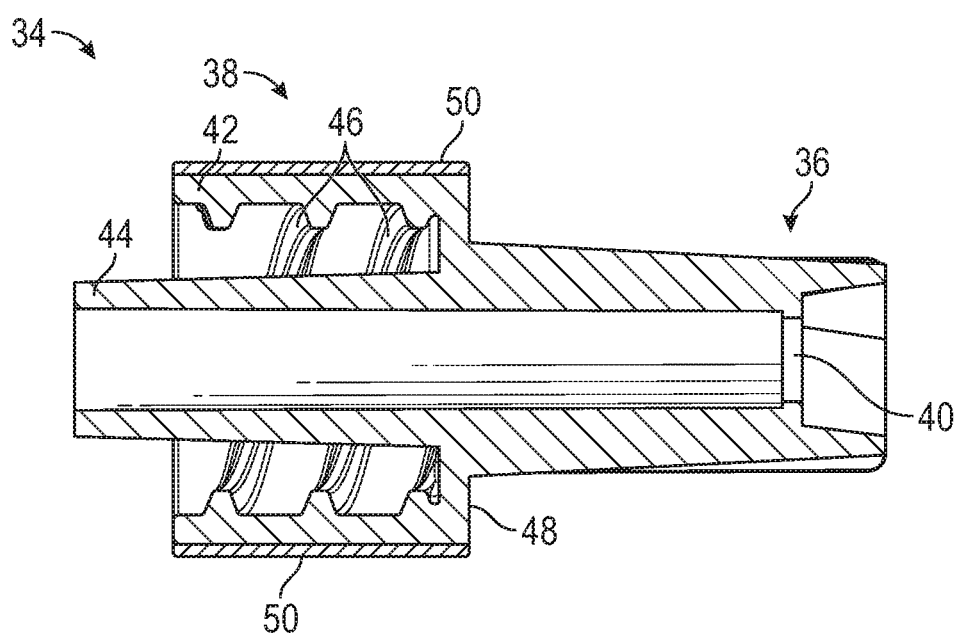
FIG. 3C is a cross-sectional view of the threaded flow control plug of FIG. 3A, along the line 3C-3C of FIG. 3B, according to some embodiments.
Figure 4A:
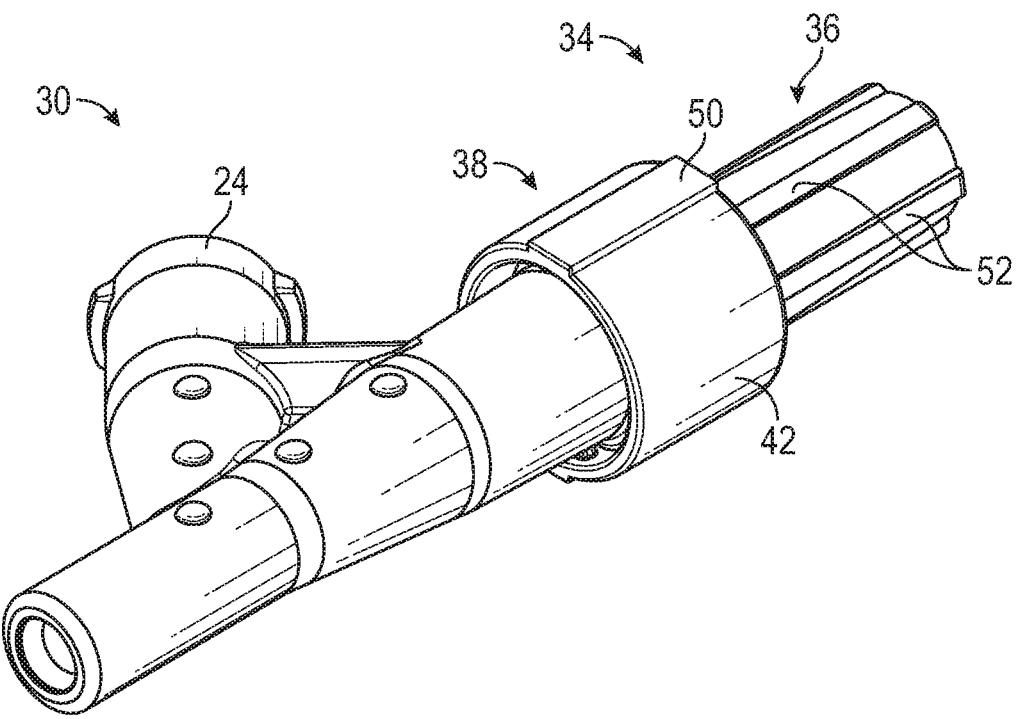
FIG. 4A is an upper perspective view of the threaded luer adapter of FIG. 2A coupled to the threaded flow control plug of FIG. 3A, according to some embodiments.
Figure 4B:
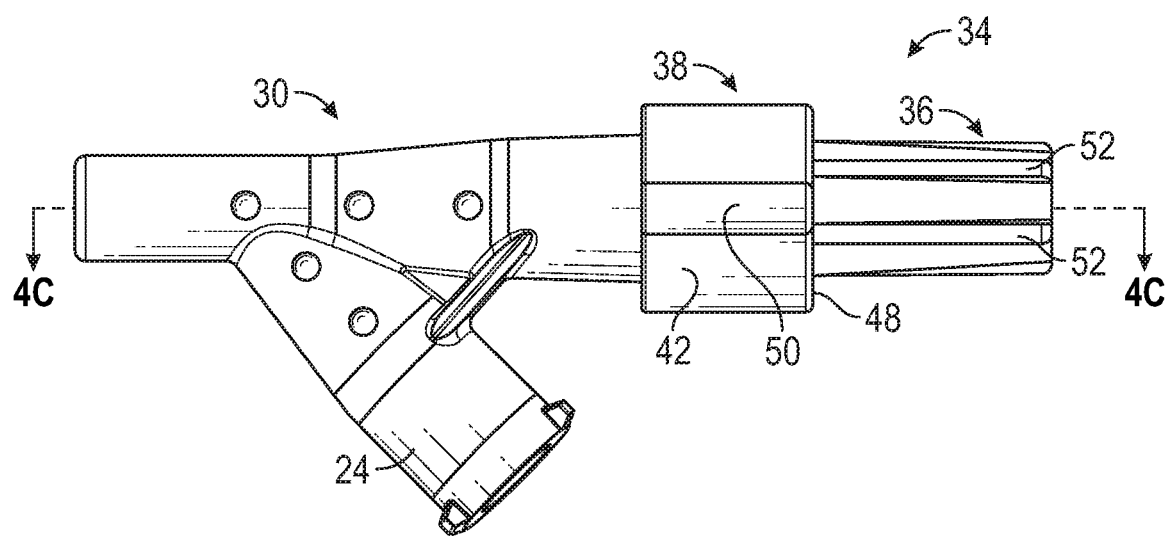
FIG. 4B is a top view of the threaded luer adapter of FIG. 2A coupled to the threaded flow control plug of FIG. 3A, according to some embodiments.
Figure 4C:
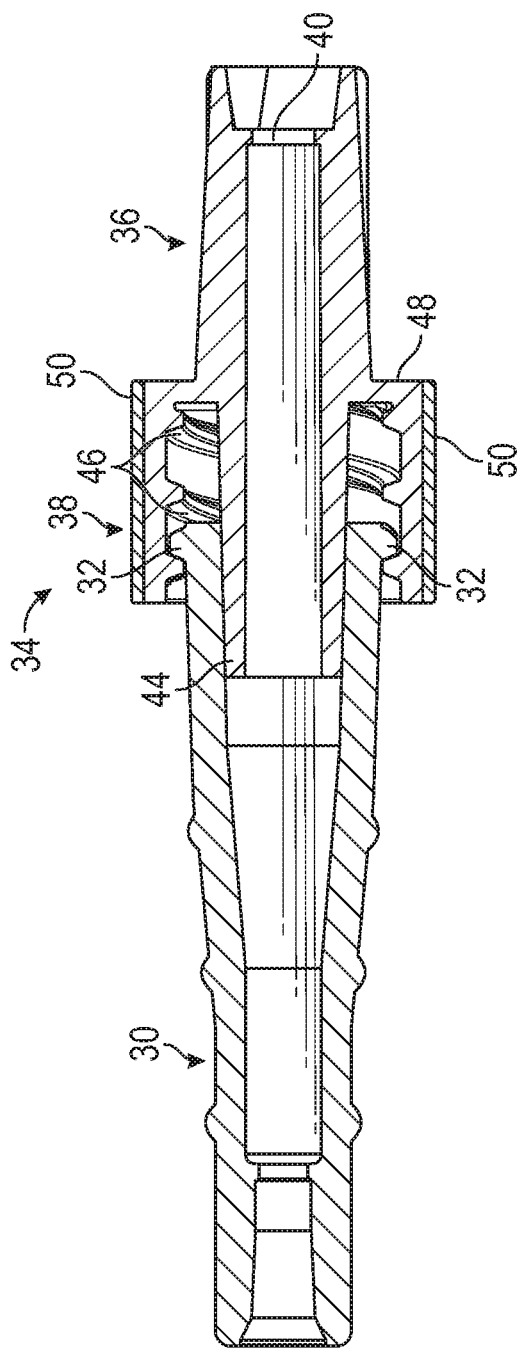
FIG. 4C is a cross-sectional view, along the line 4C-4C of FIG. 4B, of the threaded luer adapter of FIG. 2A coupled to the threaded flow control plug of FIG. 3A, according to some embodiments.
Figure 4D:
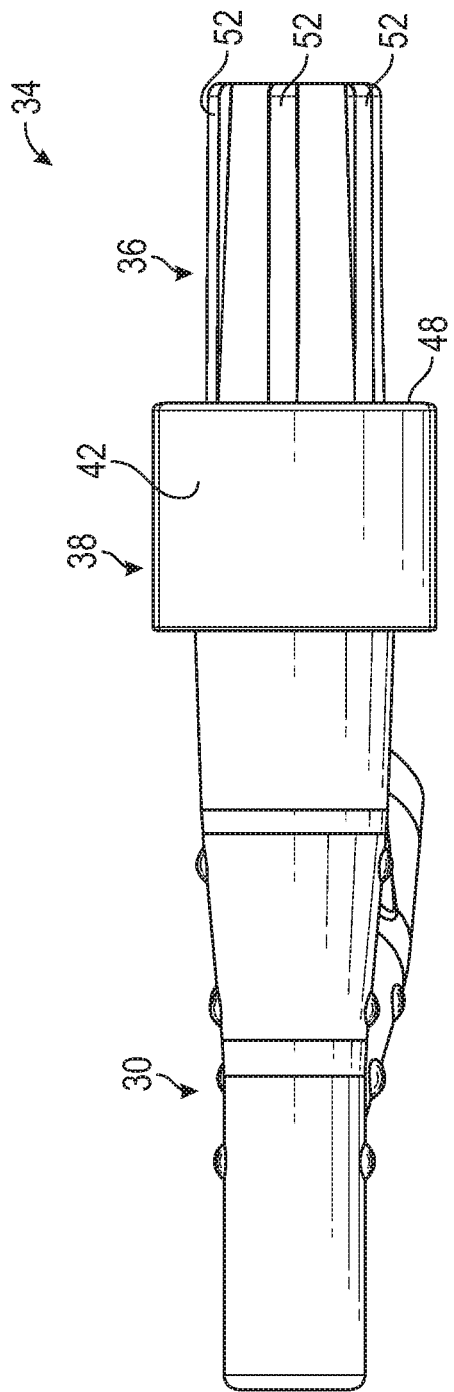
FIG. 4D is a side view of the threaded luer adapter of FIG. 2A coupled to the threaded flow control plug of FIG. 3A, according to some embodiments.

Referring now to FIG. 3A-3C, the catheter system 10 may include a flow control plug 34, which may be configured to couple to the Y-adapter 30, for example. In some embodiments, the flow control plug 34 may be removably coupled to the Y-adapter 30. In some embodiments, the flow control plug 34 may include a proximal end 36 and a distal end 38. In some embodiments, the proximal end 36 of the flow control plug, which may include a venting or filter element 40. In some embodiments, the filter element 40 may be gas permeable. In some embodiments, the filter element 40 may be permeable to air and not permeable to blood. In some embodiments, the distal end 38 may include a luer-lock portion, which may include a cylinder 42, although the luer-lock portion may also be generally cylindrical in some embodiments. In some embodiments, the distal end 38 may include the cylinder 42 and a taper-shaped luer tip 44 spaced apart from the cylinder 42.

In some embodiments, the cylinder 42 and the luer tip 44 may be sized and configured to connect to a female luer fitting. In some embodiments, the luer tip 44 may extend distal to a distal end of the cylinder 42. In some embodiments, an inner surface of the cylinder 42 may include one or more corresponding threads 46, which may be mated with the threads 32 to secure the flow control plug 34 to the Y-adapter 30. In some embodiments, the distal end 38 may include a stepped surface 48. In some embodiments, the distal end 38 may extend outwardly from the proximal end 36 to form the stepped surface 48. In some embodiments, the stepped surface 48 may be annular.

In some embodiments, an outer surface of the cylinder 42 may include one or more first grip elements 50. In some embodiments, the first grip elements 50 may include ribs, which may be oriented longitudinally with respect to the flow control plug 34, as illustrated in FIGS. 3A-3B. In some embodiments, the first grip elements 50 may extend from the stepped surface 48. In some embodiments, the first grip elements 50 may extend along an entire length of the cylinder 42, as illustrated, for example, in FIGS. 3A-3B, which may facilitate gripping of the distal end 38 by the user. In some embodiments, the first grip elements 50 may extend along a portion of a length of the cylinder 42.

In some embodiments, an outer surface of the proximal end 36 may include one or more second grip elements 52. In some embodiments, the second grip elements 52 may include ribs, which may be oriented longitudinally with respect to the flow control plug 34. In some embodiments, the cylinder 42 may include a first number of the first grip elements 50 and/or the outer surface of the proximal end 36 may include a second number of the second grip elements 52. In some embodiments, the second number may be greater than the first number. In some embodiments, having a greater number of second grip elements 52 than first grip elements 50 may facilitate placement of a palm of a hand of the user around the proximal end 36 while a thumb of the hand is placed on the distal end 38 during coupling and/or uncoupling of the Y-adapter 30 and the flow control plug 34. In some embodiments, the proximal end 36 may include 6 to 8 second grip elements 52, which may be spaced apart around a circumference of the proximal end 36. In some embodiments, a width of each of the first grip elements 50 may be greater than a width of each of the second grip elements 52, which may facilitate gripping by the thumb. In some embodiments, the first grip elements 50 may oppose each other, as illustrated, for example, in FIG. 3C, which may facilitate gripping of the distal end 38 by the thumb of the user.

In some embodiments, the filter element 40 may include a filter paper. In some embodiments, the filter element 40 may include an acrylic copolymer membrane cast on a nonwoven nylon support. In these and other embodiments, the filter element 40 may include a VERSAPOR™ 800R membrane or another suitable membrane. In some embodiments, the filter element 40 may be oleophobic and/or hydrophobic material. In some embodiments, the filter element may not leak water when subjected to 5 psi minimum water pressure for 10 seconds. In some embodiments, a rate of air flow through the filter element 40 may be between 5 cc/min and 50 cc/min when subjected to 0.1 psi or 1.0 psi air pressure. In some embodiments, the filter element 40 may be attached to the proximal end of the flow control plug 34.

In some embodiments, the flow control plug 34 may be sterilized and coupled to the Y-adapter 30. The catheter system 10, including the flow control plug 34 coupled to the Y-adapter 30, may then be packaged and shipped to a destination, such as, for example, a hospital, clinic, or other facility. In some embodiments, securement of the flow control plug 34 to the Y-adapter 30 as outlined in the present disclosure may prevent the flow control plug 34 from loosening and/or falling off the Y-adapter 30 during shipment, which might otherwise occur due to due to aging or unsecure attachment of the flow control plug 34 to the Y-adapter 30. In some embodiments, securement of the flow control plug 34 to the Y-adapter 30 as outlined in the present disclosure may avoid premature uncoupling of the flow control plug 34 from the Y-adapter 30 and subsequent contamination of the flow control plug, making the flow control plug unable to be used.

In some embodiments, the flow control plug 34 may be constructed of one or more plastic materials such as, for example, polycarbonate, polypropylene, polyethylene, glycol-modified polyethylene terephthalate, acrylonitrile butadiene styrene, or any other moldable plastic material used in medical devices. In some embodiments, the flow control plug 34 may have a melting temperature of 130° C. In some embodiments, the flow control plug 34 may be compliant with ISO 594-1.

Referring now to FIGS. 4A-4D, in some embodiments, the threads 32 of the Y-adapter 30 may be mated with the corresponding threads 46 of the flow control plug 34 to secure the flow control plug 34 to the Y-adapter 30. In some embodiments, a maximum outer diameter of the distal end 38 or cylinder 42 may be greater than a maximum diameter of the proximal end 36 (which may include the second grip elements 52 protruding from a surface of the proximal end), which may facilitate gripping of the flow control plug 34 by the user. In some embodiments, the proximal end 36 may be generally cylindrical. In some embodiments, the proximal end 36 may be tapered, as illustrated, for example, in FIG. 4C.

Figure 5A:
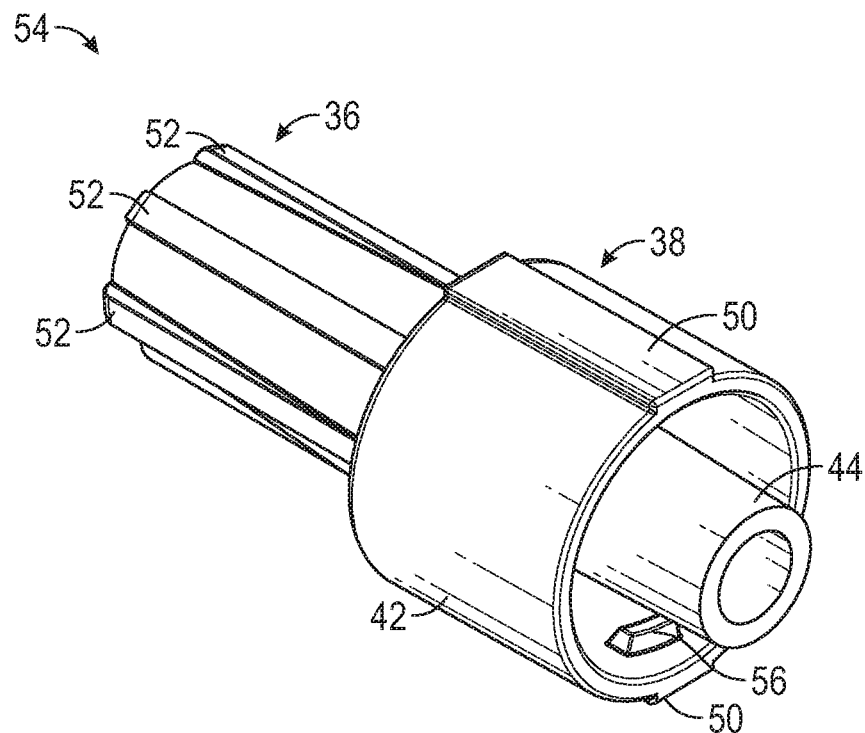
FIG. 5A is an upper perspective view of another flow control plug, according to some embodiments.
Figure 5B:
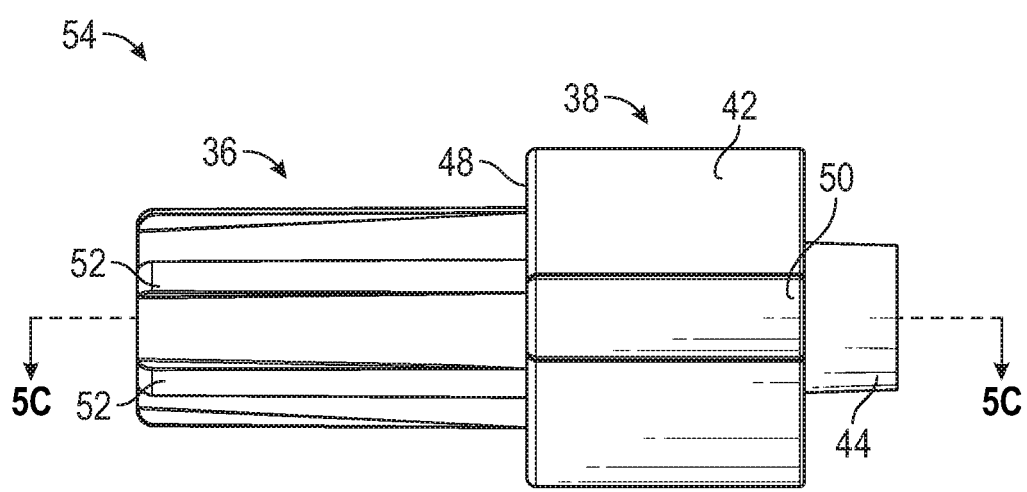
FIG. 5B is a top view of the flow control plug of FIG. 5A, according to some embodiments.
Figure 5C:
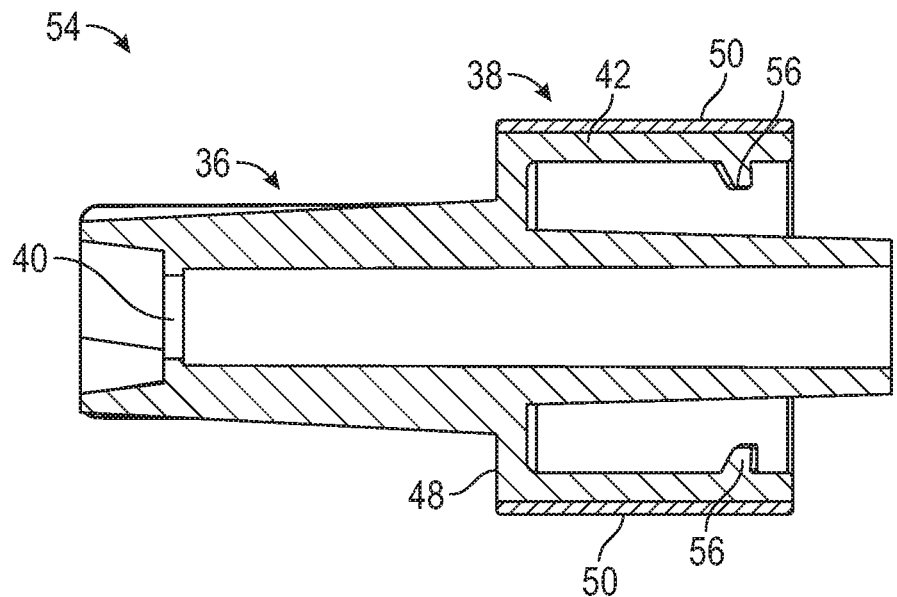
FIG. 5C is a cross-sectional view of the flow control plug of FIG. 5A, along the line 5C-5C of FIG. 5B, according to some embodiments.
Figure 6A:
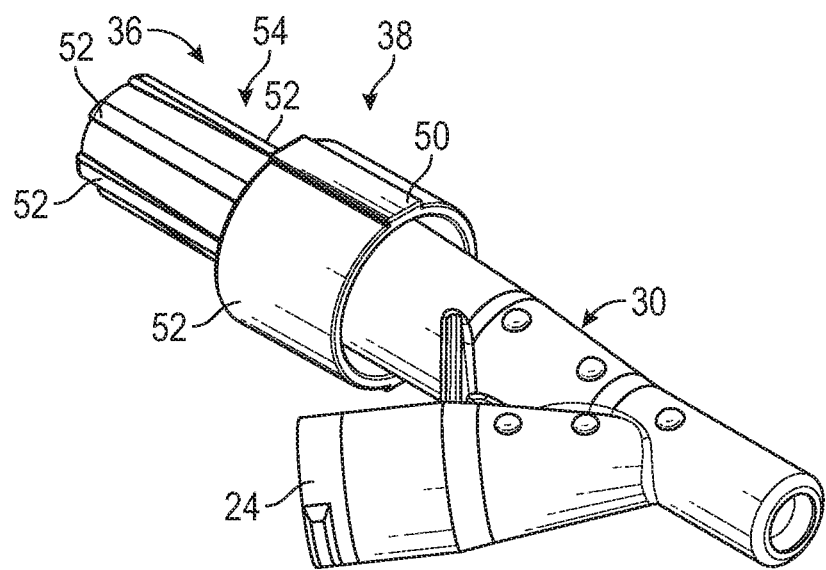
FIG. 6A is an upper perspective view of the flow control plug of FIG. 5A coupled with another luer adapter, according to some embodiments.
Figure 6B:
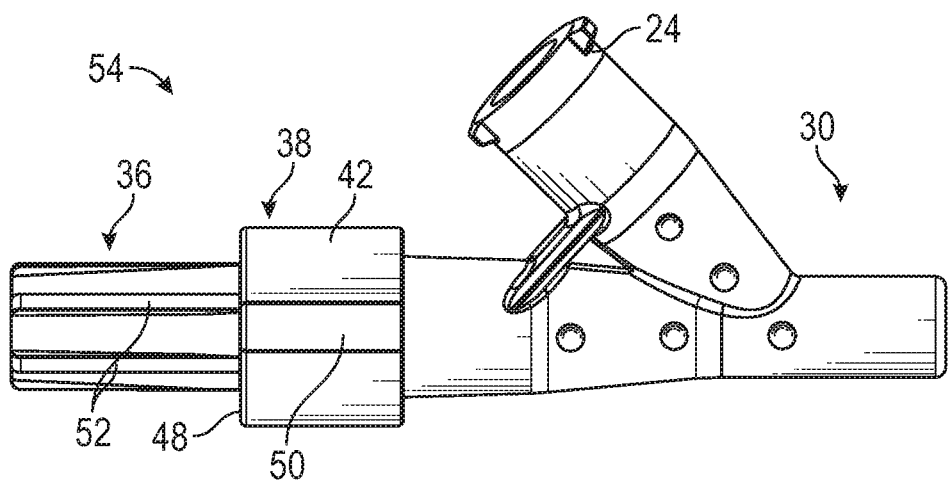
FIG. 6B is a top view of the flow control plug of FIG. 5A coupled with the other luer adapter of FIG. 6A, according to some embodiments.
Figure 6C:
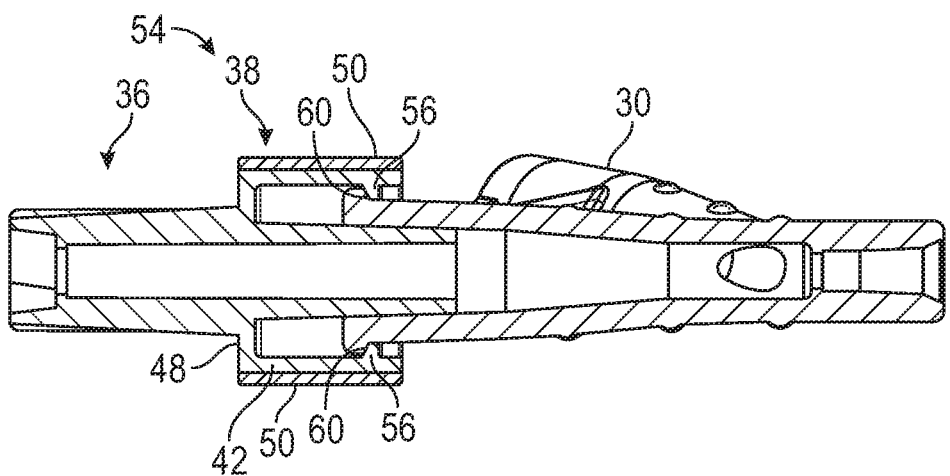
FIG. 6C is a cross-sectional view, along the line 6C-6C of FIG. 6B, of the flow control plug of FIG. 5A coupled with the other luer adapter of FIG. 6A, according to some embodiments.
Figure 6D:
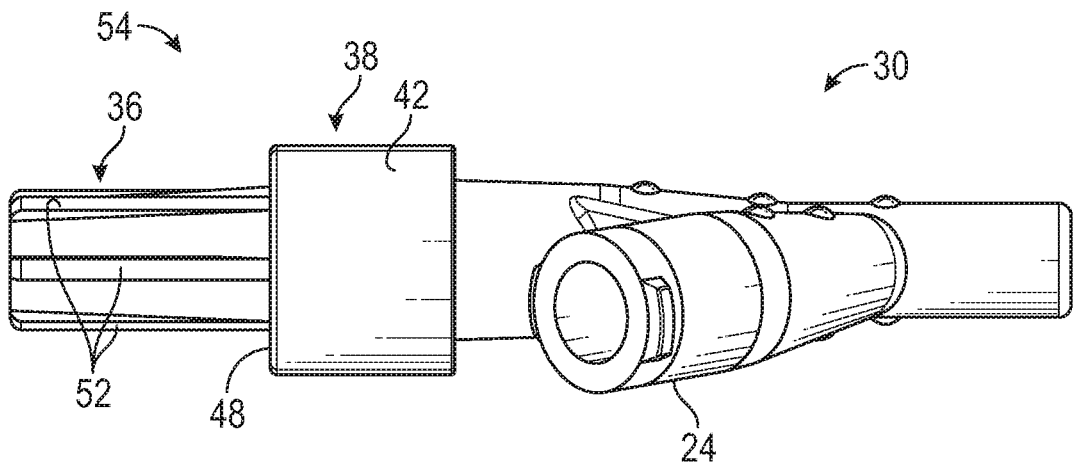
FIG. 6D is a side view of the flow control plug of FIG. 5A coupled with the other luer adapter of FIG. 6A, according to some embodiments.
Figure 7A:
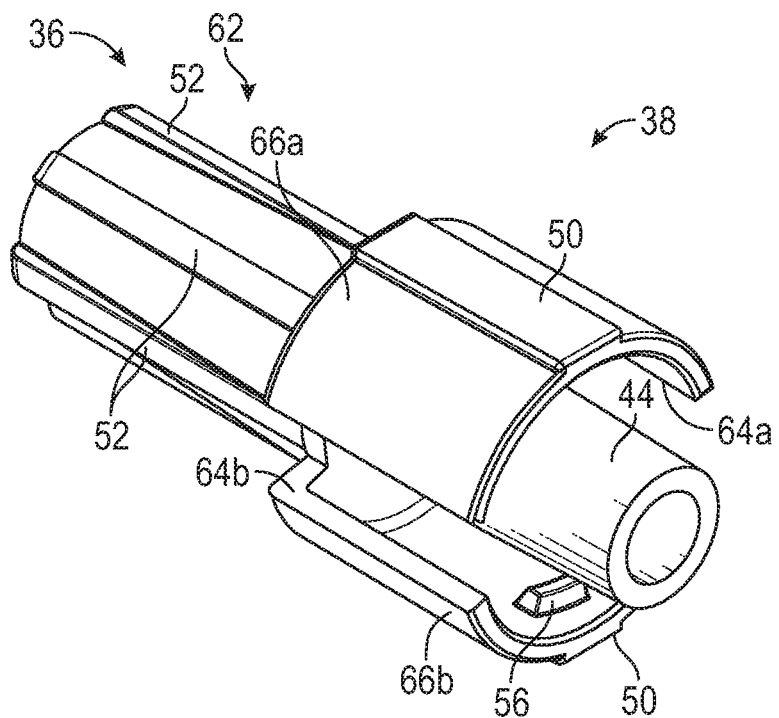
FIG. 7A is an upper perspective view another example flow control plug, according to some embodiments.
Figure 7B:
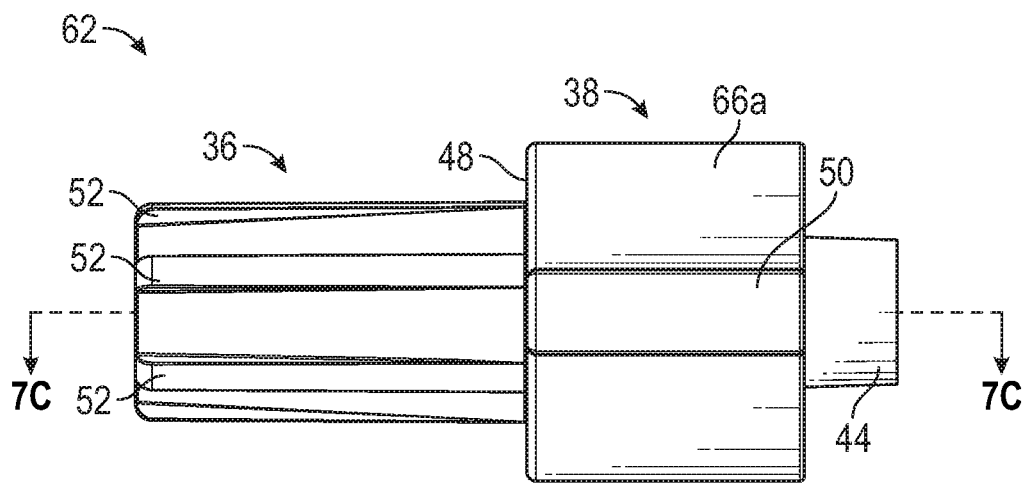
FIG. 7B is a top view of the flow control plug of FIG. 7A, according to some embodiments.
Figure 7C:
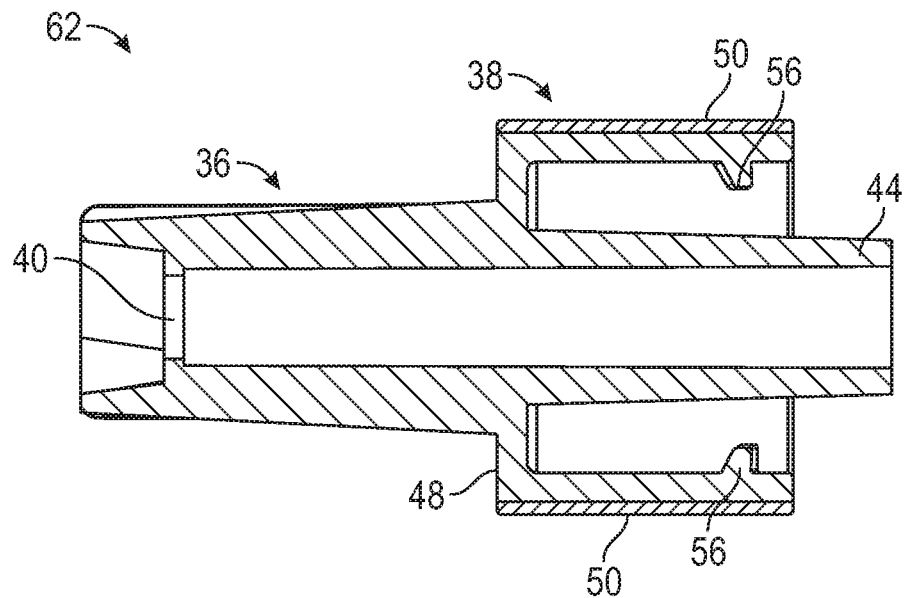
FIG. 7C is a cross-sectional view of the flow control plug of FIG. 7A, along line 7C-7C of FIG. 7B, according to some embodiments.
Figure 7D:
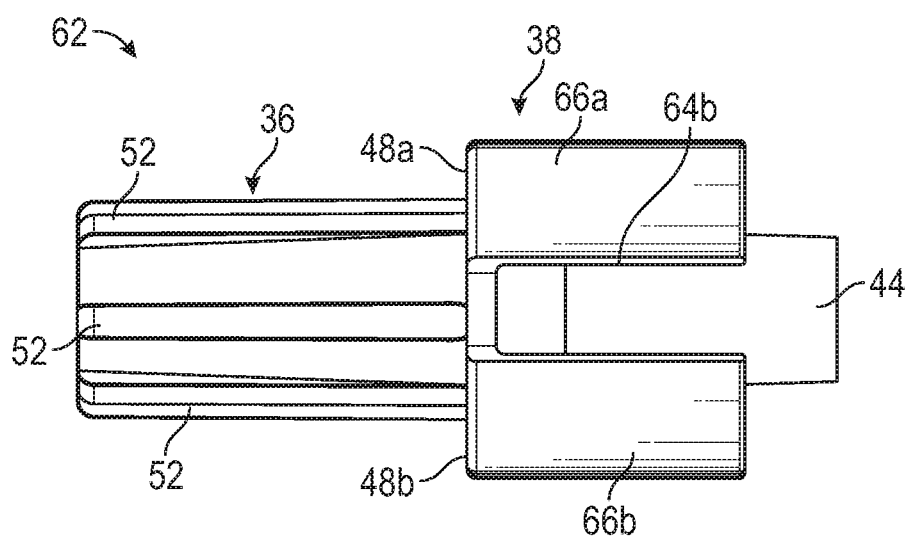
FIG. 7D is a side view of the flow control plug of FIG. 7A, according to some embodiments.
Figure 8A:
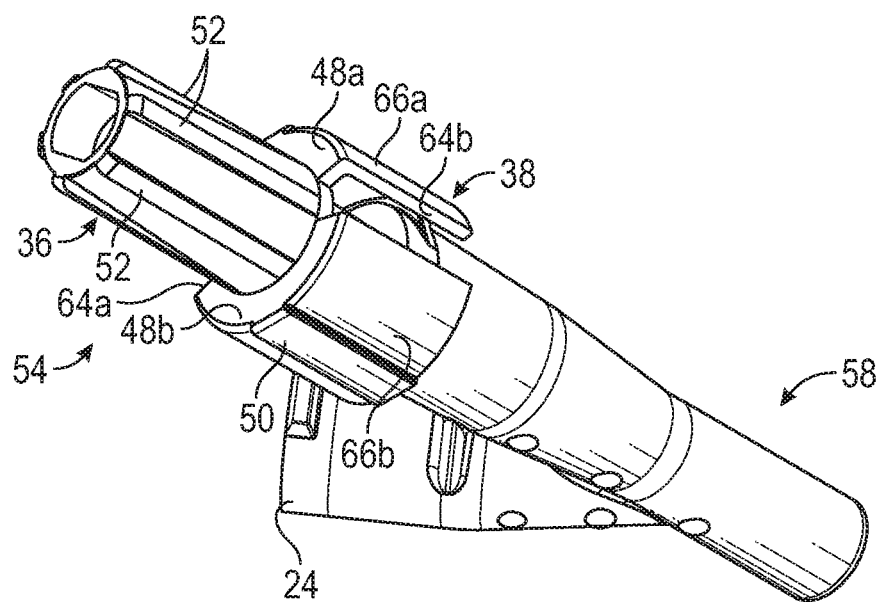
FIG. 8A is an upper perspective view of the flow control plug of FIG. 7A coupled with the other luer adapter of FIG. 6A, according to some embodiments.
Figure 8B:
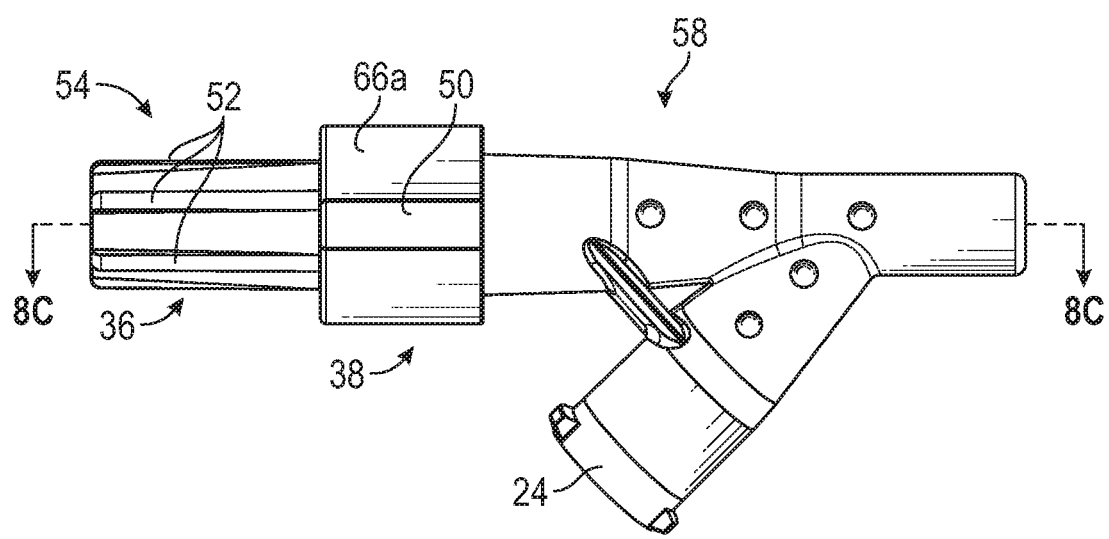
FIG. 8B is a top view of the flow control plug of FIG. 7A coupled with the other luer adapter of FIG. 6A, according to some embodiments.
Figure 8C:
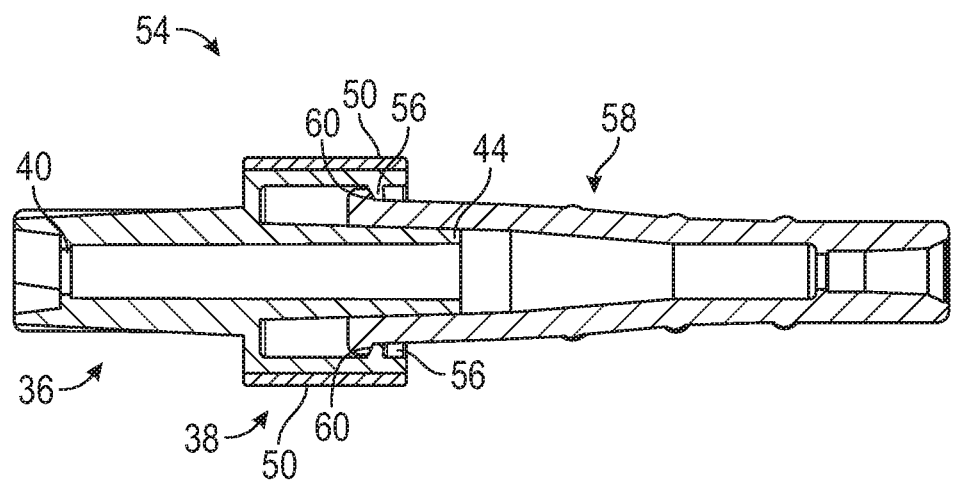
FIG. 8C is a cross-sectional view, along the line 8C-8C of FIG. 8B, of the flow control plug of FIG. 7A coupled with the other luer adapter of FIG. 6A, according to some embodiments.
Figure 8D:
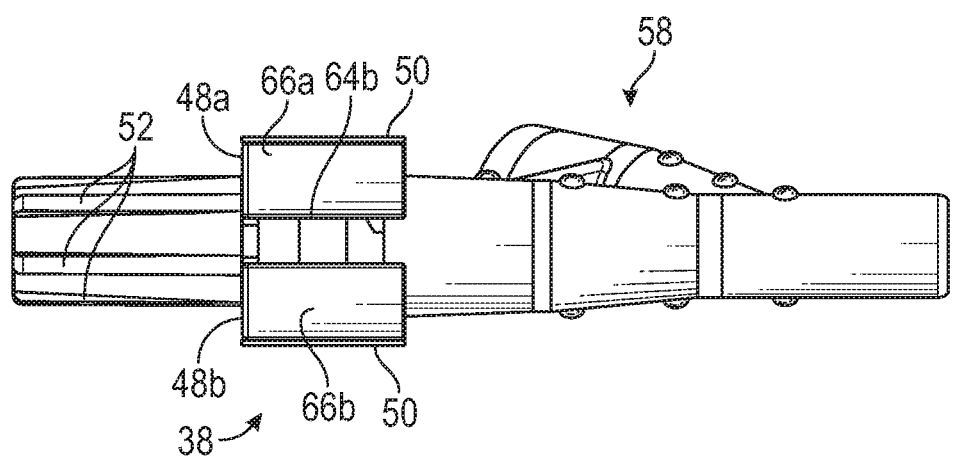
FIG. 8D is a side view of the flow control plug of FIG. 7A coupled with the other luer adapter of FIG. 6A, according to some embodiments.

Referring now to FIGS. 5A-5C, in some embodiments, the cylinder 42 of another flow control plug 54 may include an inner surface having one or more protrusions 56, which may engage in a snap-fit with another Y-adapter, such as, for example, the Y-adapter 54 illustrated in FIGS. 6A-6C. The protrusions 56 may include various shapes and sizes. In some embodiments, the inner surface of the cylinder 42 may include one or more annular protrusions 56. In some embodiments, the protrusions 56 may include ribs or flanges. In some embodiments, the flow control plug 54 may include or correspond to the flow control plug 34 of FIGS. 3-4. In further detail, in some embodiments, the flow control plug 54 may include one or more features of the flow control plug 34. For example, the flow control plug 54 may include the first grip elements 50 and/or the second grip elements 52. As another example, the proximal end 36 of the flow control plug 54 may include the filter element 40.

Referring now to FIGS. 6A-6D, in some embodiments, in some embodiments, the protrusions 56 may engage in a snap-fit with one or more recesses 60 of a Y-adapter 58, securing the flow control plug 54 to the Y-adapter 58. In some embodiments, the recesses 60 may include various shapes and sizes configured to receive the protrusions 56 in a snap-fit. In some embodiments, the recesses 60 may each include a groove. In some embodiments, a particular recess 60 may be formed by a ridge or flange and may receive one or more particular protrusions 56 in a snap-fit. In some embodiments, the ridge may be annular. In some embodiments, the flow control plug 34 may be removably coupled to the Y-adapter 58 such that the snap-fit may be undone.

Referring now to FIGS. 7A-7D, in some embodiments, the cylinder 42 of another flow control plug 62 may include one or more slots 64, which may form multiple arms 66 of the cylinder 42. The arms 66 may be disposed between the slots 64. In some embodiments, the slots 64 may extend at least partially through the cylinder 42. In some embodiments, the slots 64 may be generally aligned with a longitudinal axis of the flow control plug 62. In some embodiments, each of the arms 66 may form a curved portion of a wall of the cylinder 42. In some embodiments, the stepped surface 48 may be divided into multiple sections by the slots 66.

In some embodiments, the slots 64 and the arms 66 may facilitate engagement of the protrusions 56 and the recesses 60 in a snap-fit as the arms 66 bias outwardly when the flow control plug is moved towards the Y-adapter, allowing the protrusions 56 to more easily access the recesses 60. In some embodiments, the slots 64 may not extend through the stepped surface 48. In some embodiments, the slots 64 may extend through the stepped surface 48 and be proximate the proximal end 36, which may allow the arms 66 to bias outwardly more easily when the flow control plug 62 is being coupled to the Y-adapter 58. In some embodiments, the slots 64 may reduce a force necessary to engage the protrusions 56 and the recesses 60 in a snap-fit. In some embodiments, ends of the protrusion 56 may be spaced apart from edges of the particular arm 66 on which the protrusion 56 is disposed, giving the protrusion 56 a length that may reduce a force necessary to remove the flow control plug 54 from the Y-adapter 54 and/or couple the flow control plug 54 to the Y-adapter 54.

In some embodiments, the flow control plug 62 may include or correspond to the flow control plug 34 of FIGS.

3-4 and/or the flow control plug 54 of FIGS. 5-6. In further detail, in some embodiments, the flow control plug 62 may include one or more features of the flow control plug 54 and/or the flow control plug 34. For example, the flow control plug 62 may include the first grip elements 50 and/or the second grip elements 52. As another example, the proximal end 36 of the flow control plug 62 may include the filter element 40. Also, the flow control plug 34 and/or the flow control plug 54 may include one or more features of the flow control plug 62.

In some embodiments, an inner surface of one or more of the arms 66 may include a particular protrusion 56, which may engage in a snap-fit with a particular recess 60. In some embodiments, the distal end 38 may include a first slot 64a and a second slot 64b (which may be referred to herein collectively as "slots 64"), and the arms 66 may include a first arm 66a and a second arm 66b (which may be referred to herein collectively as "arms 66"), as illustrated, for example, in FIG. 7A. In some embodiments, the first slot 64a and the second slot 64b may be disposed between the first arm 66a and the second arm 66b. In some embodiments, the stepped surface 66a may be proximate the first arm 66a and/or the stepped surface 66b may be proximate the second arm 66a, as illustrated, for example, in FIG. 7A.

In some embodiments, an inner surface of the first arm 66a may include a first protrusion 56. In some embodiments, an inner surface of the second arm 66b may include a second protrusion 56. In some embodiments, the first protrusion 56 may oppose the second protrusion 56. In some embodiments, the first and second protrusions 56 may be engaged in a snap-fit with a single recess 60 or with multiple recesses 60 disposed on the outer surface of the Y-adapter 58.

Referring now to FIGS. 8A-8D, in some embodiments, the protrusions 56 may engage in a snap-fit with one or more recesses 60 of the Y-adapter 58, securing the flow control plug 54 to the Y-adapter 58. In some embodiments, any adapter may be used to connect two or more vascular access devices may be used in place of the Y-adapter 58. It is understood that in some embodiments, the inner surface of the cylinder 42 or the inner surface of the arms 66 may include one or more recesses 60, while the outer surface of the Y-adapter 58 may include one or more protrusions 56.

In some embodiments, the flow control plug 54 and/or the flow control plug 62 may be sterilized and coupled to the Y-adapter 58. The catheter system 10, including the flow control plug 54 or the flow control plug 62 coupled to the Y-adapter 58, may then be packaged and shipped to a destination, such as, for example, a hospital, clinic, or other facility. In some embodiments, securement of the flow control plug 54 and/or the flow control plug 62 to the Y-adapter 58 as outlined in the present disclosure may prevent the flow control plug 54 and/or the flow control plug 62 from loosening and/or falling off the Y-adapter 58 during shipment, which might otherwise occur due to due to aging or unsecure attachment of the flow control plug 54 and/or the flow control plug 62 to the Y-adapter 58.

In some embodiments, a method of securing a flow control plug to a catheter system for shipment may include providing the catheter system. In some embodiments, the method may include sterilizing and/or coupling the flow control plug to a luer adapter of the catheter system before shipping the catheter system to a destination. In some embodiments, coupling the flow control plug to the luer adapter of the catheter system before shipping the catheter system to the destination includes engaging the recess with the protrusion in a snap-fit or mating the threading to the corresponding threading.

The present invention may be embodied in other specific forms without departing from its structures, methods, or other essential characteristics as broadly described herein and claimed hereinafter. The described embodiments and examples are to be considered in all respects only as illustrative, and not restrictive. The scope of the invention is, therefore, indicated by the appended claims, rather than by the foregoing description. All changes that come within the meaning and range of equivalency of the claims are to be embraced within their scope.

All examples and conditional language recited herein are intended for pedagogical objects to aid the reader in understanding the invention and the concepts contributed by the inventor to furthering the art, and are to be construed as being without limitation to such specifically recited examples and conditions. Although implementations of the present inventions have been described in detail, it should be understood that the various changes, substitutions, and alterations could be made hereto without departing from the spirit and scope of the invention.

The invention claimed is:

1. A catheter system, comprising:
   a luer adapter, comprising an outer surface having a recess, wherein the luer adapter is coupled to a catheter adapter via extension tubing;
   a flow control plug, comprising:
      a proximal end having a filter element permeable to air and not to blood; and
      a distal end having a cylinder and a taper-shaped luer tip spaced apart from the cylinder, wherein an inner surface of the cylinder includes a protrusion engaged in a snap-fit with the recess, wherein an outer surface of the distal end comprises a plurality of first ribs and an outer surface of the proximal end comprises a plurality of second ribs, wherein the plurality of first ribs and the plurality of second ribs are oriented longitudinally with respect to the flow control plug, wherein the outer surface of the proximal end has more second ribs than the outer surface of the distal end has first ribs, and wherein the distal end further comprises a stepped surface, wherein the distal end extends outwardly from the proximal end to form the stepped surface, wherein the stepped surface is annular.

2. The catheter system of claim 1, wherein the luer adapter is a Y-adapter.

3. The catheter system of claim 1, wherein the plurality of first ribs extend from the stepped surface and along an entire length of the cylinder.

4. The catheter system of claim 1, wherein a width of each of the plurality of first ribs is greater than a width of each of the plurality of second ribs.

5. The catheter system of claim 1, wherein the plurality of first ribs comprises a first rib and a second rib that opposes the first rib.

* * * * *